US006367706B1

(12) United States Patent
Putz

(10) Patent No.: US 6,367,706 B1
(45) Date of Patent: Apr. 9, 2002

(54) FRAGRANCE EXTENDING DEVICE AND METHOD THEREFOR

(76) Inventor: Larry J. Putz, 2120 Barberry Ave., Grand Junction, CO (US) 81506

( * ) Notice: Subject to any disclaimer, the term of this patent is extended or adjusted under 35 U.S.C. 154(b) by 0 days.

(21) Appl. No.: 09/114,009

(22) Filed: Jul. 10, 1998

(51) Int. Cl.[7] ................................................. A61L 9/04
(52) U.S. Cl. ........................ 239/6; 239/44; 239/51.5; 239/53
(58) Field of Search ........................ 239/34, 44, 51.5, 239/53, 55, 56, 57, 326

(56) References Cited

U.S. PATENT DOCUMENTS

| | | | | |
|---|---|---|---|---|
| 4,921,636 A | * | 5/1990 | Traas ........................... | 239/44 |
| 5,304,358 A | * | 4/1994 | Hoyt et al. .................... | 239/56 |
| 5,383,598 A | * | 1/1995 | Styles ........................... | 239/57 |
| 5,556,030 A | * | 9/1996 | Paul ............................. | 239/56 |
| 5,573,984 A | * | 11/1996 | Breitenbucher et al. ...... | 501/39 |

* cited by examiner

*Primary Examiner*—Lisa Ann Douglas
(74) *Attorney, Agent, or Firm*—Timothy J. Martin; Michael R. Henson; Mark H. Weygandt

(57) ABSTRACT

A fragrance extender releases fragrance from a fragrance producing composition over a prolonged interval of time. The fragrance includes a piece of ceramic material of sufficient porosity to permit penetration of the fragrance emitting substance and the carrier liquid therefor. A support structure supports the piece of material relative to a support surface so that the exposed surface area that receives the fragrance emitting substance is at a removed location. A method of retarding the evaporation of a selected fragrance producing composition is also disclosed. The method includes the steps of providing a piece of ceramic material and then contacting a portion of the exposed surface of the ceramic material with the selected composition.

22 Claims, 2 Drawing Sheets

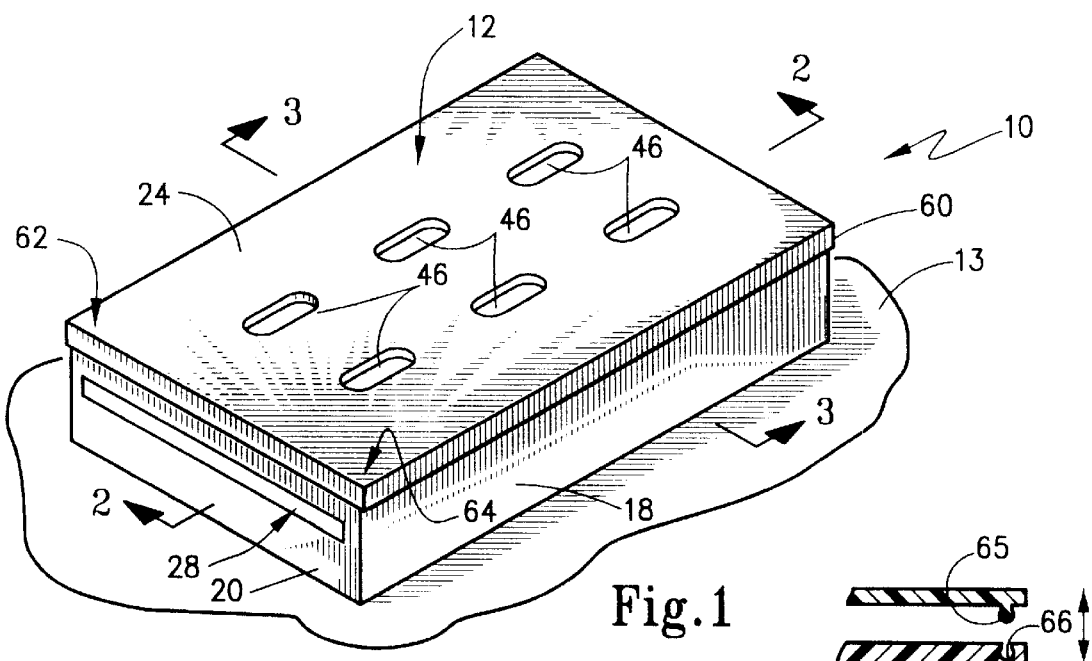
Fig. 1
Fig. 4
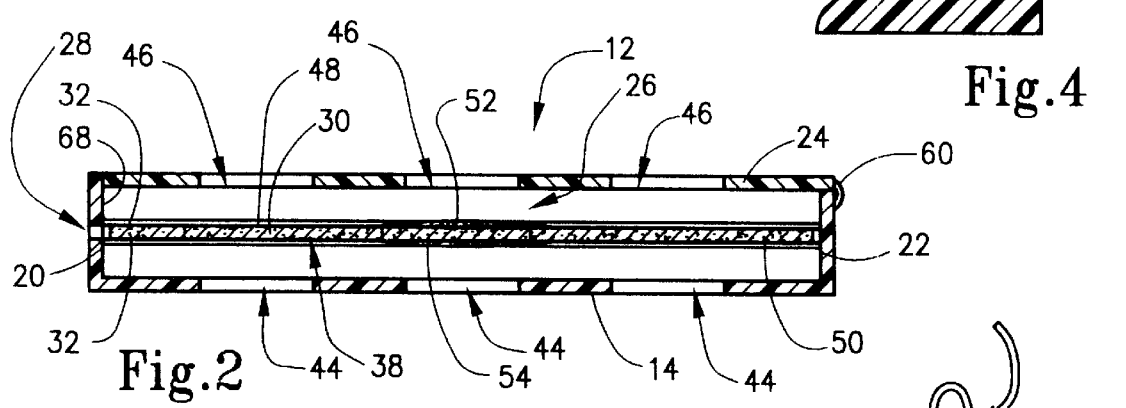
Fig. 2
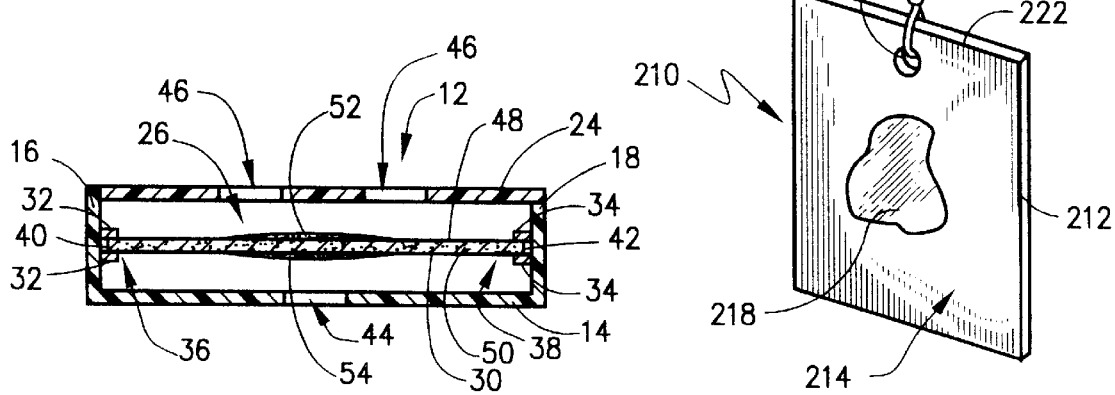
Fig. 3
Fig. 8

FRAGRANCE EXTENDING DEVICE AND METHOD THEREFOR

FIELD OF THE INVENTION

The present invention broadly concerns fragrance emitting devices. More particularly, however, the present invention is directed to a device which controls the emission of a selected fragrance so as to prolong the interval of time over which the fragrance may be detected by the olfactory senses. Thus, the present invention is also directed to a method for extending the interval of time for which a fragrance may be perceived by the senses.

BACKGROUND OF THE INVENTION

While often less appreciated then other ones of the senses, the sense of smell has great importance both to the well-being and pleasure of existence. Various fragrances and odors are pervasive throughout the environment so that the sense of smell plays an important role in the interaction of an organism with this environment. The importance of the sense of smell exists in the detection of both pleasant and unpleasant odors.

A sense of smell can protect the organism against dangerous situations. For example, the smell of smoke can alert a human or other animal to the threat of fire. Likewise, the detection of different gases or other chemicals can serve to warn against impending danger. The detection, by the sense of smell, of tainted or spoiled food can protect the human or other animal against the ingestion of a substance that may cause sickness or death.

However, on the more pleasant side, the sense of smell enhances the enjoyment of the environment. The fragrance of flowers, plants and other organic materials can instill satisfaction and pleasure. Indeed, it has been determined that the sense of smell is actually a large component of that which is referred to as the sense of taste. Moreover, the sense of smell plays an important role in sexual attraction among animals and is essential to the reproductive cycles of many plants.

Since many people enjoy the presence of pleasant fragrances, humans have long sought to bring pleasant odors into their environment. For example, men and women alike adorn themselves with a plethora of fragrances, both to please themselves as well as others with whom they come in contact. Fragrances are used in many toiletry products, such as lotions, deodorants, shaving compositions, soaps and the like. The perfume industry alone is a multi-billion dollar enterprise.

Pleasant fragrances are also used to enhance the air or, alternatively, to mask less pleasant odors. For example, there are fiber board pads, often in a decorative shape, which are impregnated with various odors so that they may be hung in closets, automobiles and other confined spaces. These devices emit their fragrance over an interval of time after which they are typically discarded. Other devices mount into electrical outlets and use electricity to stimulate the emission of a fragrance. Another popular product is referred to as "potpourri" which is typically a mixture of dried pedals, leaves or other organic materials that are placed in an exposed container so that the fragrance of the organic materials permeates the air. Potpourri may also be encased in a cloth-like material to result in a sachet. Sachets are often placed in drawers, such as lingerie drawers, to lend a fragrance to the clothing surrounding the sachet.

A disadvantage of existing devices is that they typically may not be personalized to a particular user. That is, consumer selection is confined to a relatively limited number of available fragrances that have been pre-packaged for use. Thus, it is possible that the fragrances from such commercial products may clash with other fragrances employed by the user. For example, the odor imparted to the clothing may clash with the perfume or cologne used by the wearer of the clothing.

However, it has not heretofore been a simple matter for a person to use his or her own cologne or perfume in the manner of a sachet. Colognes and perfumes are typically either alcohol based or oil based and, regardless of their carrier liquid, are rather quick to evaporate. Therefore, although the fragrance is readily detectable, it only lasts for a rather short duration of time. Furthermore, attempting to find a suitable substrate for an individually selected fragrance has been less than satisfactory. The present invention is directed to satisfying the long felt need for devices and methods of employing personalized fragrances over an extended period of time.

SUMMARY OF THE INVENTION

It is an object of the present invention to provide a new and useful fragrance extending device and method which can prolong the interval of time over which a fragrance may be emitted into an ambient environment.

It is another object of the present invention to provide a device which permits the use of personalized fragrances that may be employed for individual use.

It is a further object of the present invention to provide a device which can receive a selected liquid with a personalized fragrance, which device prevents contact of the liquid from other objects in its vicinity.

Still a further object of the present invention is to provide a fragrance extending device which may be configured into a decorative item.

According to the present invention, then, a fragrance extender is adapted to be positioned relative to a support surface and is operative to receive a fragrance producing composition. Here, the fragrance producing composition includes a fragrance emitting substance in a carrier liquid. The fragrance extender releases the fragrance over a prolonged interval of time. Broadly, the fragrance extender includes a piece of porous material having sufficient porosity to prevent penetration thereof by the carrier liquid and the fragrance emitting substance. This piece has an exposed surface area that is adapted to contact a selected quantity of the fragrance producing composition at a removed location relative to the support surface. A support structure is then operative to contact the support surface and to support the piece of material relative to the support surface whereby the exposed surface area is supported at the removed location.

Preferably, the porous material is a ceramic material, especially sintered aluminum oxide. The sintered aluminum oxide preferably has a particle size of between and 4–7 micrometers, inclusively. The piece of material may have a coating disposed on the surface thereof with this coating having a window defining the exposed surface area but otherwise operative to seal the surface thereunder. This coating is preferably formed of a printable substance, such as a sublimation receptive organic polymer, which is then printed upon with a sublimated ink transfer process.

The support structure can take on a variety of forms. For example, the support structure may be selected from a group consisting of housings, pads and hangers. Where the support structure is a housing, it has a surrounding wall and an interior. The piece of porous material is then suspended within the interior. This housing may including positioning elements located in the interior that operate to suspend the piece of porous material. Moreover, where a housing is provided, the housing preferably has a plurality of ports formed into the wall to allow the escape of the fragrance. Here, also, the piece of porous material may be configured as a flat plate having opposite lateral edges. The positioning elements may be a pair of facing channel structures disposed on the surrounding wall in the interior of the housing. These channel structures are sized and oriented to slidably receive the lateral edges of the flat plate thereby to releaseably mount the flat plate in the interior of the housing.

Alternatively, the piece of porous material may be configured as a flat plate that has a first surface and a second surface opposite thereto. The support structure may be pad disposed on the second surface with this pad being, for example, a resilient foam material.

In still another embodiment, the piece of porous material may have a passageway formed therethrough, and the support structure can be an elongated piece of flexible material, such as a string, ribbon, and the like, which extends through the passageway.

The present invention is also then directed to a fragrance device that includes the porous piece of material, as described above, with a fragrance producing composition being in contact with an exposed surface area of this porous piece of material. Here, the fragrance emitting substance has a carrier liquid, and the porous material is non-chemically reactive with the carrier liquid. The fragrance producing composition is selected from a group consisting of perfumes and colognes, and the carrier liquid may be selected from a group consisting of alcohols and oils.

The method according to the present invention is that of retarding the evaporation of a selected fragrance producing composition that is in a liquid form so that the fragrance is released over a prolong interval of time. The method includes any steps contemplated by the foregoing structure. Specifically, however, the method includes the step of providing a piece of porous material having exposed surface area followed by contacting at least a portion of the exposed surface area with a quantity of the selected fragrance producing composition. In the method, the porous material may be a ceramic material, such as sintered aluminum oxide, with the aluminum oxide having a particle size of between 4–7 micrometers, inclusively, as noted above.

These and other objects of the present invention will become more readily appreciated and understood from a consideration of the following detailed description of the exemplary embodiments when taken together with the accompanying drawings, in which:

BRIEF DESCRIPTION OF THE DRAWINGS

FIG. 1 is a perspective view of a fragrance extender according to a first exemplary embodiment of the present invention;

FIG. 2 is a cross-sectional view taken about lines 2—2 of FIG. 1;

FIG. 3 is a cross-sectional view taken about lines 3—3 of FIG. 1;

FIG. 4 is a cross-sectional view showing the releasable latching structure at the corner of the housing of the fragrance emitter shown in FIG. 1;

FIG. 8 is a perspective view of a third exemplary embodiment of the present invention.

DETAILED DESCRIPTION OF THE EXEMPLARY EMBODIMENTS

Figure 5:
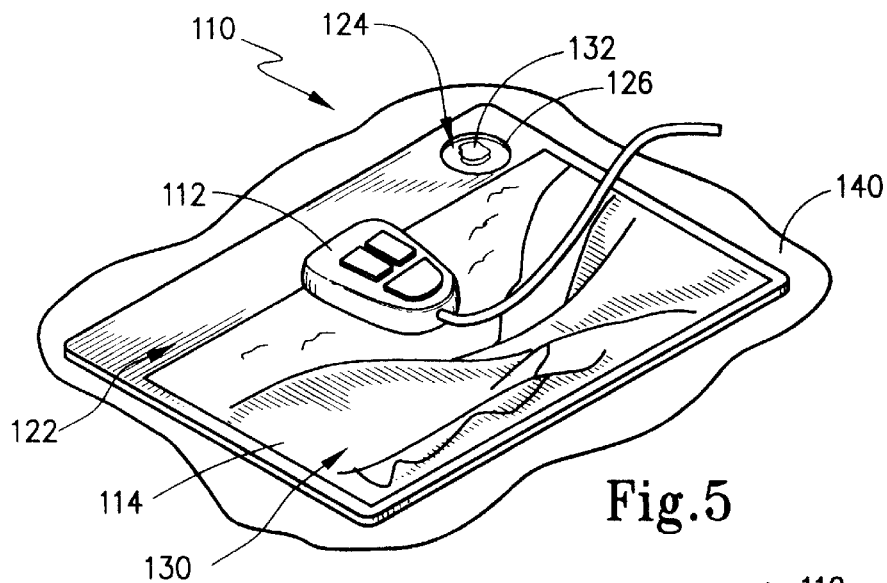
FIG. 5 is a perspective view of a second exemplary embodiment of the present invention, in the form of a computer mouse pad.

The present invention is directed to a fragrance extender that is adapted to receive a fragrance producing composition, especially a perfume or a cologne. The purpose of this device is to release the fragrance over a prolonged interval of time so that the pleasant odor may be detected long after the fragrance producing composition would otherwise have evaporated. The present invention also concerns the combination of the fragrance extending device along with a selected fragrance so that the user may have a customized fragrance device for placing in closets, clothes drawers, automobiles and other spaces as an enhancement to his/her environment. The invention is also directed to the method of extending the fragrance from such a fragrance producing composition.

Broadly, the present invention includes a porous material having sufficient porosity to permit penetration thereof by a carrier liquid that contains the fragrance emitting substance. This porous material may be a ceramic porcelain and is preferably aluminum oxide, also known as alumina. A support structure, such as a housing, pad, flexible member, etc. then supports the piece of porous material relative to a support surface so that an exposed surface area is supported at a removed location from the surface. The exposed surface area may then receive the fragrance producing composition.

A first exemplary embodiment, then, of the present invention is shown in FIGS. 1–4. With reference to FIGS. 1–3, it may be seen that fragrance device 10 includes a housing 12 which is adapted to rest on a support surface 13 and which is formed by a surrounding wall. Specifically, housing 12 includes a bottom wall 14, a pair of side walls 16 and 18, a pair of end walls 20 and 22, and a top wall 24. Housing 10 thus has an open interior 26 that is sized to receive a piece of porous material which in FIGS. 1—3 is a thin rectangular plate 30 preferably constructed of alumina, as noted above. Plate 30 is supported relative to a support surface 13. Here, plate 30 is suspended between and parallel to bottom wall 14 and top wall 24 when housing 10 is in an enclosed state as is shown in FIGS. 1–3. As such, plate 30 is suspended above support surface 13. To accomplish this, the interior surface of each of side walls 16 and 18 is provided with positioning elements in the form of a pair of ribs 32 and 34, respectively, so as to form facing channels 36 and 38. Channels 36 and 38 are sized to slidably receive lateral edges 40 and 42 of plate 30 thereby to releasably mount plate 30 in the interior 26 of housing 12. Plate 30 is thus suspended equidistantly between bottom wall 14 and top wall 24.

In order to permit insertion and removal of plate 30 from housing 12, end wall 20 is provided with a transverse slot 28 which has a width that is the same as plate 30 and a height that equals the thickness of plate 30. A plurality of bottom openings or ports 44 are formed in bottom wall 14. Similarly, a plurality of ports 46 are formed in top wall 24. Each of ports 44 and 46 are preferably oval in shape and are provided to allow circulation of air through housing 12. As is best shown in FIGS. 2 and 3, plate 30 has an upper surface 48 and a lower surface 50 that defines an exposed surface area that is adapted to receive quantities 52 and 54 of a fragrance producing composition. Ports 44 and 46 are thus provided to allow circulation of air through housing 12 so that the fragrance emitted from quantities 52 and 54 may communicate with the external environment.

In order to introduce quantities 52 and 54 onto surfaces 48 and 50, the user may simply place several drops of the composition through ports 46 and 44, respectively. Alteratively, as is shown in FIGS. 1, 2 and 41 top wall 24 defines a lid for housing 12 that is secured along a top edge of end wall 22 by a living hinge 60. Each corner 62 and 64 is provided with a releasable latching structure in order to secure top wall 24 in the closed position shown in FIGS. 1–3. With reference to FIG. 4, it may be seen that an exemplary latching structure may be comprised of a bead or knob 65 which is sized for snap-fitting engagement with a cavity 66 formed in a corner ledge 68 (FIG. 2). Knob 65 and cavity 66 are preferably tear-dropped in shape and are of complimentary size for snap-fitted engagement with one another.

Figure 6:
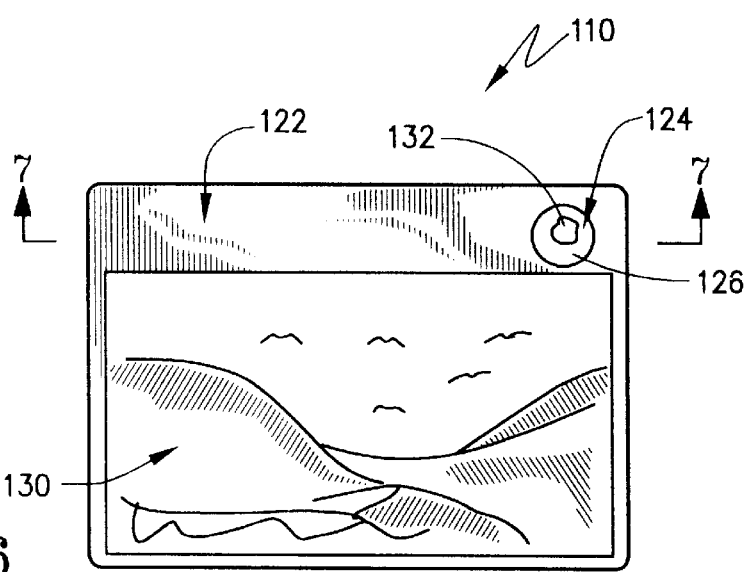
FIG. 6 is a top plan view of the fragrance emitter shown in FIG. 5.
Figure 7:
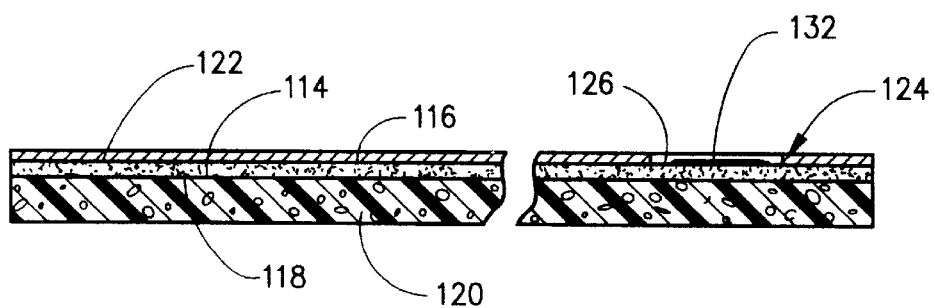
FIG. 7 is a cross-sectional view, taken about lines 7—7 of FIG. 6.

A second exemplary embodiment of the present invention is shown in FIGS. 5–7. Here, the fragrance extender device 110 is configured in the form of a rigid mouse pad constructed for use with a computer input device 112. Fragrance extender device 110 is in the form of a flat, generally rectangular piece of porous material or plate 114 which again is in the form of a sintered aluminum oxide material. An advantage of having this mouse pad as a rigid construct is that it may be used on an uneven surface, such as a person's lap, an upholstered seat, etc. that is highly advantageous when employed in conjunction with a lap top computer.

In any event, plate 114 has an upper surface 116 and a lower surface 118. A support structure is provided for plate 114. Here, the support structure is defined by a pad 120 of any suitable resilient foam material that may be preferably bonded to the second or lower surface 118. The first or upper surface 116 has a coating 122 formed thereon with this coating having an open window 124 that exposes a surface area 126 of upper surface 116. Otherwise, coating 122 operates to seal the surface 116 of plate 114. Coating 122 is preferably a printable substance, such as a sublimation receptive organic polymer that is suitable to receive a printed design such as printed decorative design 130. Window 124 is provided so that a selected quantity 132 of a fragrance producing composition may be placed directly onto the exposed surface 126.

From the foregoing, it may be appreciated that pad 120 is operative to support the exposed surface 126 at a removed location from a support surface 140.

A third exemplary embodiment of the present invention is shown in FIG. 8. Here, the fragrance extending device 210 is in the form of a rectangular plate 212 that has an exposed surface 214. Plate 212 is adapted to be supported, relative to a support structure, by means of a flexible hanger 216 of any suitable construction. Alternatively, hanger 216 could be a rigid hanger, as should be appreciated by the ordinarily skilled person in this art. To facilitate the attachment of the hanger, such as flexible hanger 216, plate 212 includes an opening or passageway 220 extending at a location proximately to an edge 222 of plate 212 at a medial location therealong. Passageway 220 allows the hanger 216 to extend therethrough and be affixed for suspending fragrance extending device 210 from any suitable support, such as in a closet, from a rear view mirror of a vehicle, etc. In any event, surface 214 of plate 212 may receive a quantity 218 of a fragrance producing composition.

As noted above, the porous material according to the preferred embodiment of the present invention is aluminum oxide or "alumina". This ceramic is of a type normally formed by roll compaction wherein spray dried alumina power having an average grain size of 4–7 micrometers is roll formed and then sintered to become a rigid plate. This fabrication process is not, however, part of the present invention as such techniques are readily known in the art. A suitable roll formed material of sintered aluminum oxide (thick film substrate tech., spec. 37-3-0897) is available from the Coors Ceramics Company of Grand Junction, Colo. This porous material should have sufficient porosity to permit penetration by the carrier liquid in the fragrance emitting substance which comprises the fragrance producing composition. To this end, it should be understood that the fragrance producing composition, which is normally a perfume or a cologne, is in a carrier liquid selected from a group consisting of alcohols and oils. In any event, it is important that the porous piece of material be one that is non-chemically reactive with the carrier liquid.

From the foregoing, it should be appreciated that the present invention is also directed to a method of retarding the evaporation of a selected fragrance producing composition that is in a liquid form so that the fragrance is released over a prolonged interval of time. This method comprises the steps of providing a piece of porous material having an exposed surface area and thereafter contacting at least a portion of the exposed surface area with a quantity of the selected fragrance producing composition. Preferably, this method is one wherein the porous material is a ceramic, namely, sintered aluminum oxide wherein the aluminum oxide has a particle size of between 4–7 micrometers, inclusively. Further, it should be understood that this method includes any step contemplated by the structure described above.

Accordingly, the present invention has been described with some degree of particularity directed to the exemplary embodiments of the present invention. It should be appreciated, though, that the present invention is defined by the following claims construed in light of the prior art so that modifications or changes may be made to the exemplary embodiments of the present invention without departing from the inventive concepts contained herein.

I claim:

1. A method of retarding the evaporation of a selected fragrance producing composition that is in a liquid form so that the fragrance is released over a prolonged interval of time, comprising the steps of:

(a) providing a piece of ceramic material having sintered aluminum oxide as a major constituent thereof and having an exposed surface area; and (b) contacting at least a portion of the exposed surface area with a quantity of the selected fragrance producing composition.

2. The method according to claim 1 wherein said ceramic is sintered aluminum oxide.

3. The method according to claim 1 wherein said aluminum oxide has a particle size of between 4–7 micrometers, inclusively.

4. A fragrance extender adapted to be positioned relative to a support surface and operative to receive a fragrance producing composition that includes a fragrance emitting substance in a carrier liquid whereby the fragrance is released over a prolonged interval of time, comprising:

(a) a piece of ceramic material having sufficient porosity to permit penetration thereof by the carrier liquid and the fragrance emitting substance, said piece having an exposed surface area adapted to contact a selected quantity of the fragrance producing composition at a removed location relative to the support surface; and (b) a support structure operative to contact the support surface and to support said piece of material relative to the support surface whereby the exposed surface area is supported at the removed location.

5. A fragrance extender according to claim 4 wherein said ceramic is sintered aluminum oxide.

6. A fragrance extender according to claim 5 wherein said aluminum oxide has a particle size of between 4–7 micrometers, inclusively.

7. A fragrance extender according to claim 4 wherein said support structure is selected from a group consisting of housings, pads and hangers.

8. A fragrance extender according to claim 4 wherein said support structure is a housing having a surrounding wall and an interior, said piece of porous material being suspended within the interior.

9. A fragrance extender according to claim 8 wherein said housing has a plurality of ports formed in the wall.

10. A fragrance extender according to claim 4 wherein said piece of porous material is configured as a flat plate having a first surface and a second surface opposite said first surface, said support structure being a pad disposed on the second surface.

11. A fragrance extender according to claim 4 wherein said piece of porous material has a passageway formed therethrough, said support structure being an elongated piece of flexible material extending through the passageway.

12. A fragrance device operative to emit a selected fragrance over a protracted interval of time, comprising:

(a) a fragrance producing composition including a fragrance emitting substance that emits the selected fragrance and a carrier liquid therefor; and (b) a piece of a ceramic material that is non-chemically reactive with the carrier liquid, said piece having an exposed surface area, said fragrance producing composition being in contact with the exposed surface area.

13. A fragrance device according to claim 12 wherein said composition is selected from a group consisting of perfumes and colognes.

14. A fragrance device according to claim 13 wherein said carrier liquid is selected from a group consisting of alcohols and oils.

15. A fragrance extender adapted to be positioned relative to a support surface and operative to receive a fragrance producing composition that includes a fragrance emitting substance in a carrier liquid whereby the fragrance is released over a prolonged interval of time, comprising:

(a) a piece of a porous material having sufficient porosity to permit penetration thereof by the carrier liquid and the fragrance emitting substance, said piece having a coating disposed on a surface thereof and operative to seal the surface thereunder, said coating having a window defining an exposed surface area adapted to contact a selected quantity of the fragrance producing composition at a removed location relative to the support surface; and (b) a support structure operative to contact the support surface and to support said piece of material relative to the support surface whereby the exposed surface area is supported at the removed location.

16. A fragrance extender according to claim 15 wherein said coating is a printable substance.

17. A fragrance extender according to claim 16 wherein said coating is a sublimation receptive organic polymer.

18. A fragrance extender adapted to be positioned relative to a support surface and operative to receive a fragrance producing composition that includes a fragrance emitting substance in a carrier liquid whereby the fragrance is released over a prolonged interval of time, comprising:

(a) a piece of a porous material configured as a flat plate having opposite lateral edges and having sufficient porosity to permit penetration thereof by the carrier liquid and the fragrance emitting substance, said piece having an exposed surface area adapted to contact a selected quantity of the fragrance producing composition at a removed location relative to the support surface; and (b) a support structure forming a housing having a surrounding wall and an interior and operative to contact the support surface and to support said piece of material relative to the support surface whereby the exposed surface area is supported at the removed location, said support structure including a pair of facing channel structures disposed on said wall in the interior, said channel structures sized and oriented to slidingly receive said lateral edges thereby to releasably mount said flat plate in the interior of said housing thereby to suspend said piece of porous material within the interior.

19. A fragrance extender according to claim 18 wherein said housing has a plurality of ports formed in the wall.

20. A fragrance extender adapted to be positioned relative to a support surface and operative to receive a fragrance producing composition that includes a fragrance emitting substance in a carrier liquid whereby the fragrance is released over a prolonged interval of time, comprising:

(a) a piece of a porous material configured as a flat plate having a first surface and a second surface opposite said first surface and having sufficient porosity to permit penetration thereof by the carrier liquid and the fragrance emitting substance, said piece having an exposed surface area adapted to contact a selected quantity of the fragrance producing composition at a removed location relative to the support surface; and (b) a pad disposed on the second surface and operative to contact the support surface and to support said piece of material relative to the support surface whereby the exposed surface area is supported at the removed location.

21. A fragrance extender according to claim 20 including a coating disposed on the first surface, said coating having a window formed therein to define the exposed surface area.

22. A fragrance extender according to claim 21 including a decorative design printed on said coating.

* * * * *